Figure 1:
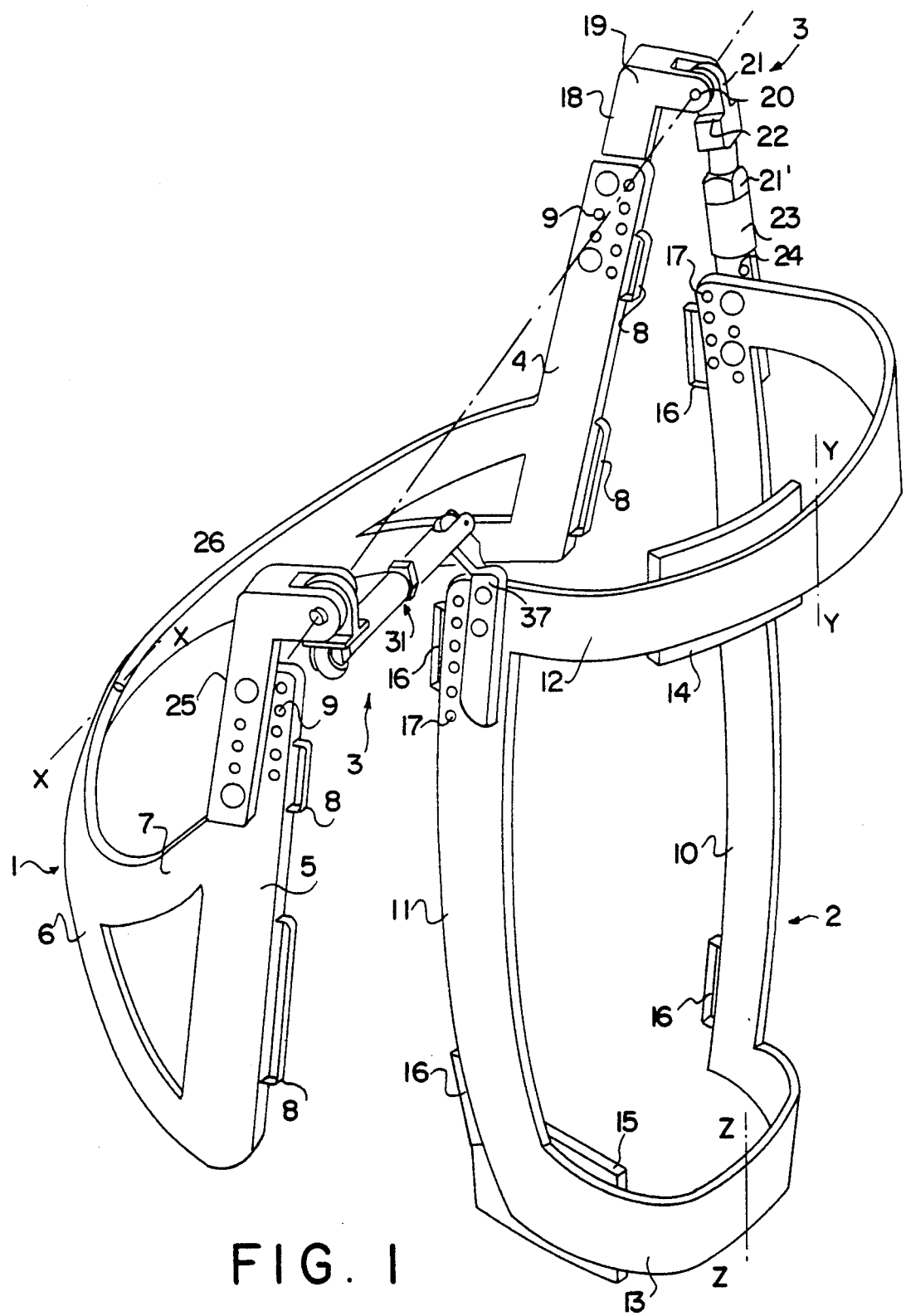

United States Patent [19]
Cadoret

[11] Patent Number: 5,119,805
[45] Date of Patent: Jun. 9, 1992

[54] ORTHOPEDIC APPARATUS FOR INSTABLE KNEES

[76] Inventor: Alain J. Cadoret, 71 rue de Starnberg, 35800 Dinard, France

[21] Appl. No.: 667,007

[22] Filed: Mar. 11, 1991

Related U.S. Application Data

[63] Continuation of Ser. No. 533,939, Jun. 4, 1990, abandoned, which is a continuation of Ser. No. 420,646, Oct. 11, 1989, abandoned, which is a continuation of Ser. No. 273,661, Nov. 18, 1988, abandoned, which is a continuation of Ser. No. 162,326, filed as PCT/FR87/00235, Jun. 19, 1987, published as WO87/07828, Jun. 19, 1987, abandoned.

[30] Foreign Application Priority Data

Jun. 20, 1986 [FR] France .................. 86 9062

[51] Int. Cl.$^5$ .................. A61F 3/00; A61F 5/00; A61F 5/10
[52] U.S. Cl. .................. 602/16; 602/26
[58] Field of Search .................. 128/80 C, 80 F, 80 G, 128/80 H, 88

[56] References Cited

U.S. PATENT DOCUMENTS

| | | | |
|---|---|---|---|
| 3,885,252 | 5/1975 | Nakajima | 128/80 C |
| 4,271,831 | 6/1981 | Deibert | 128/80 C |
| 4,463,751 | 8/1984 | Bledsoe | 128/80 C |
| 4,614,181 | 9/1986 | Karlsson | 128/80 C |
| 4,681,097 | 7/1987 | Pansiera | 128/77 |
| 4,733,656 | 3/1988 | Marquette | 128/80 C |
| 4,751,920 | 6/1988 | Mauldin et al. | 128/80 C |
| 4,817,588 | 4/1989 | Bledsoe | 128/80 C |

FOREIGN PATENT DOCUMENTS 673387 11/1963 Canada .................. 128/80 C

Primary Examiner—Edgar S. Burr
Assistant Examiner—Kimberly Asher
Attorney, Agent, or Firm—Laff, Whitesel, Conte & Saret

[57] ABSTRACT

The apparatus has a thigh retaining component (1) and a leg retaining component (2) tied together by an articulation apparatus (3).

The external articulation is formed of two legs (18 and 21-23-24) articulated as a knee brace to block forward extension.

The external articulation has an upper articulated leg (25), set as a knee brace, with the upper part of a cross piece (27) whose lower portion is articulated at the end of a rod (31) whose other end is articulated to the lower leg (37).

The leg (21-23-24) and the rod (31) are, preferably adjustable in length and their ends can turn slightly with respect to one another.

The brace of the invention can be advantageously used in almost all cases of knee instability while allowing it good freedom of motion.

15 Claims, 4 Drawing Sheets

ORTHOPEDIC APPARATUS FOR INSTABLE KNEES

This application is a continuation of application Ser. No. 07/533,939, now abandoned, filed Jun. 4, 1990, now abandoned, which was a continuation of Ser. No. 07/420,646 filed Oct. 11, 1989, which was a continuation of Ser. No. 07/273,661 filed Nov. 18, 1988, now abandoned, which was a continuation of Ser. No. 07/162,326, filed as PCT/FR87/00235, Jun. 19, 1987, published as WO87/07828, Jun. 19, 1987 now abandoned.

The present invention relates to an orthopedic apparatus for a knee which is unstable as a result of ligamentary, articular, neurological or muscular injuries.

Chronic deficiencies of the knee are handicapping in a general way, and more specifically for certain professional or sport activities.

Through re-education, we can mitigate the deficiency of the ligaments by making the periarticular muscles work hard in a controlled manner. We also allow the capsular, ligamentary and the muscular sensors to respond immediately to any dangerous articular motion in order that a reflex contraction of the periarticular muscles stops the motion.

A well carried out re-eduation allows a good functional recuperation, even in cases where abnormal movement predicted by a clinical examination is considerable. However, the re-education has its limits which are quickly reached during certain activities such as high level sports.

In the presence of a chronically unstable knee which surgery and re-education cannot improve further, there remains the solution of reducing one's physical activity in relation to the remaining functional possibilities or that of providing a brace to mitigate the capsule-ligamentary deficiency while hindering the normal operation of the knee in the least possible manner.

Such braces exist, such as the simple elastic knee holder band, the strapping type bands or single axis motion apparatus. Although satisfactory, the efficiency of strapping is too low for strenuous requirements. With regards to the apparatus with a single axis of motion, they are rarely prescribed because, since their axis does not exactly correspond with that of the knee, they have a tendency to slip on the lower member during repeated bends. Thus a binding to the shoes or the belt through a swivel pin is necessary, which is very constraining.

The motion of the knee is in fact very complex. For example, during one bend, the motion of a point of the frontal-inside of the tibia with respect to a point of the internal condyle is broken down into a rotation around the bending-extension of the knee, a translation in the frontal-backside corresponding to a forward motion of the tibia under the condyles, a translation corresponding to the difference in the bending radius of the touching surfaces during motion and a small varus displacement.

A number of articulation systems reproducing a number of the motion components of the knee have been imagined. Such a system has been described in French patent document FR-A-2 477 407. The articulation is monocentric but a portion of the external support is soft to allow some rotation of the leg with respect to the thigh.

In document FR-A-2 546 743, the articulation reproduces the sliding and rotation motion of the knee.

Of course, these braces reproduce only part of the motion of the knee and do not allow motion in all the physiological segments of the knee. It is much too complex to have the axis of a simple mechanical system correspond exactly with that of the knee throughout its motion during a bending or an extension.

In French patent application No. 78 32598, the present applicant has foreseen an articulated system which is passively controlled by the knee itself, except in non-physiological segments which avoids the calculation of the articulation centres. The brace is made up of a retention system fixed to the thigh and the leg and a movement system for the two sides of the knee. With regards to the leg component of the retention system, some bending is allowed with some movements which do not affect the efficiency of the brace. The brace well respects the physiology of the knee. It is light and comfortable. It is however, a bit cumbersome and does not meet all the needs. In particular, it is not provided with a setting for the valgus-varus.

However, such setting shows multiple interesting facets. It allows the efficient adaption of the brace to each morphology by very precisely setting its axis. It allows setting of the tension on the valgus or the varus or counteraction against valgus or varus deformations either rheumatoid, neurological or muscular. During the post-surgical phase, it provides a means to constrain the lateral movements for the healing period of the ligaments operated upon without necessitating the immobilizing of the knee. Furthermore, it allows articular discharge, either on the internal or the external side, to limit single compartment hyperpressure of arthrosis origin due to a lack of an axis.

It may also be interesting to limit the ending-extension, especially if the brace is used for the post-surgery phase. For example, if we limit the extension to $-20°$ and the flexion to $60°$, we avoid any tension on the ligamentary sutures, all while allowing some mobility to the knee.

One object of the present invention is therefore to provide a knee-brace with adjustability of the valgus-varus and, possibly, of the bending extension.

Another object of the invention is to seek a simple, sturdy and least cumbersome mechanical system.

Another object of the invention is to improve the leg and thigh retaining apparatus.

In accordance with a characteristic of the invention, the brace has a thigh retaining component having an internal and an external mount connected by a brace, a leg retaining element also having internal and external mounts connected by at least one brace, the internal mounts and the external mounts being connected by two lateral articulations respectively, the external articulation having two legs articulated into a knee-brace to block extension towards the front, the internal articulation having an upper leg articulated around a slightly traversal axis, according to a knee arrangement, with the upper part of a cross-piece whose lower part is articulated at the end of a rod, the other end of which is articulated to the lower part of the internal articulation according to an antero-posterior axis.

In accordance with another characteristic of the invention, the lateral articulations are a thread type.

In accordance with another characteristic of the invention, at least one of the legs of the external articulation and of the rod of the internal articulation is made up of two parts, one of which has a threaded shank engaged into a threaded end of the other part, to facilitate the setting of their length.

In accordance with another characteristic of the invention, on the threaded shanks of the leg and of the rods, are arranged lock nuts limiting or blocking the rotation of one of their parts with respect to the other part.

In accordance with another characteristic of the invention, the braces of the thigh restraining component end of the leg restraining component are articulated in their center part, to adapt themselves to varying muscular volumes or to movements of the tibia or the fibula during various movements.

In accordance with another characteristic of the invention, the leg restraining component has two braces.

In accordance with another characteristic of the invention, the thigh restraining component has triangulation bars between its brace and its mounts.

In accordance with another characteristic of the invention, support surfaces made of soft material are attached to the internal sides of the leg braces.

In accordance with another characteristic of the invention, the soft support surfaces are obtained through casting directly on the leg of the subject.

In accordance with another characteristic of the invention, the lower support area is hooked to the upper part of the frames.

In accordance with another characteristic of the invention, the articulations have means to limit the extension or the bending of the brace.

To further increase the comfort and efficiency of the brace, one can provide, between the framework of the thigh restraining component and the thigh itself, attachment parts which, on one hand, have a large contact area with the thigh and, on the other hand, allow the framework of the said restraining component a given small freedom of motion in the axis of the thigh.

In accordance with another characteristic of the invention, the thigh restraining component has an upper attachment part with a front band, provided with a soft cover, wider than the brace, fixed to the ends of the brace, the end attachment, on the internal side, allowing a slight longitudinal motion of the brace with respect to the thigh, and a lower attachment part having a front band, provided with a soft cover, whose part on the inside of the thigh, has a coupling sleeve with an axis somewhat parallel to that of the thigh, in which goes a restraining component through the internal mount of the thigh, the opening of the sleeve having a width larger than that of the mount, such that it can move freely either towards the front on the back, as well as longitudinally with respect to the thigh, the said front band passing, on the other side, in a loop tied to the exterior side of the external mount, the front bands of the upper and lower attachment parts being extended, to their limits, by straps provided with tightening and tying means.

In accordance with another characteristic of the invention, the upper attachment part has in its central part a sleeve through which passes the brace, the width of the opening of the sleeve being greater than that of the brace such that it can slightly move longitudinally with respect to the thigh.

In accordance with another characteristic of the invention the binding straps are elastic.

In accordance with another characteristic of the invention, the front band of the lower binding part has notches for freeing the knee-cap.

Figure 2:
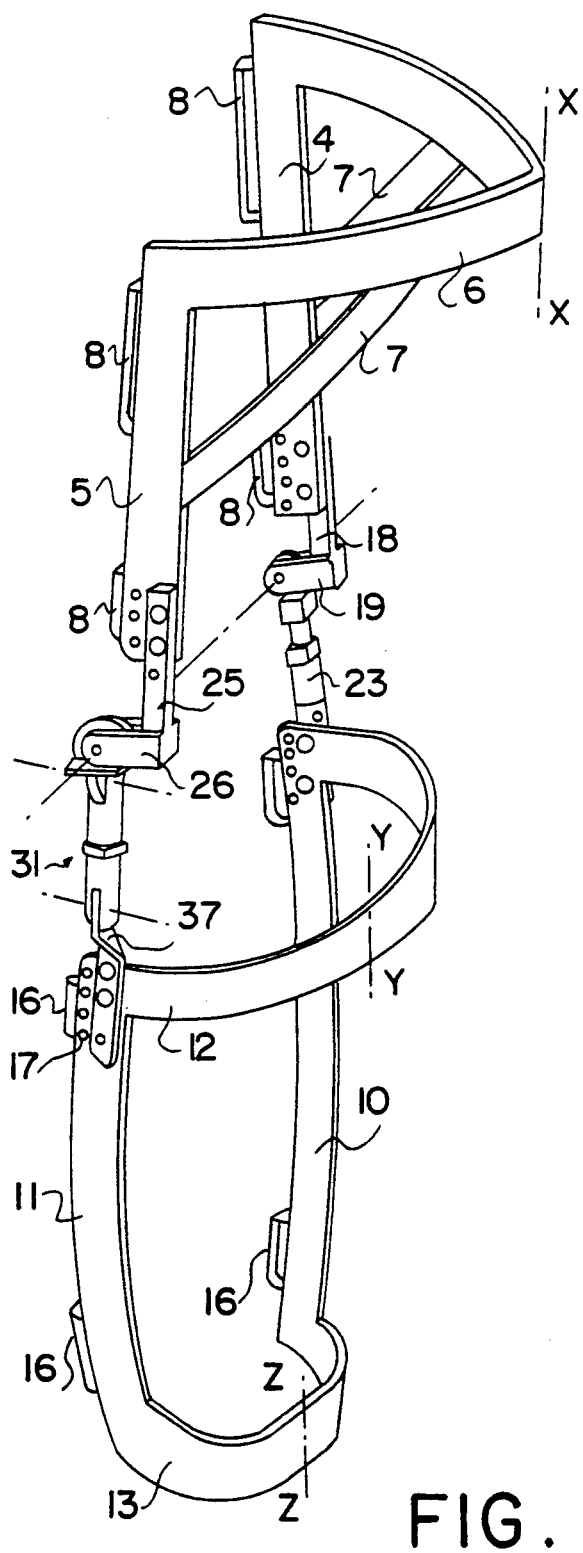
Figure 3:
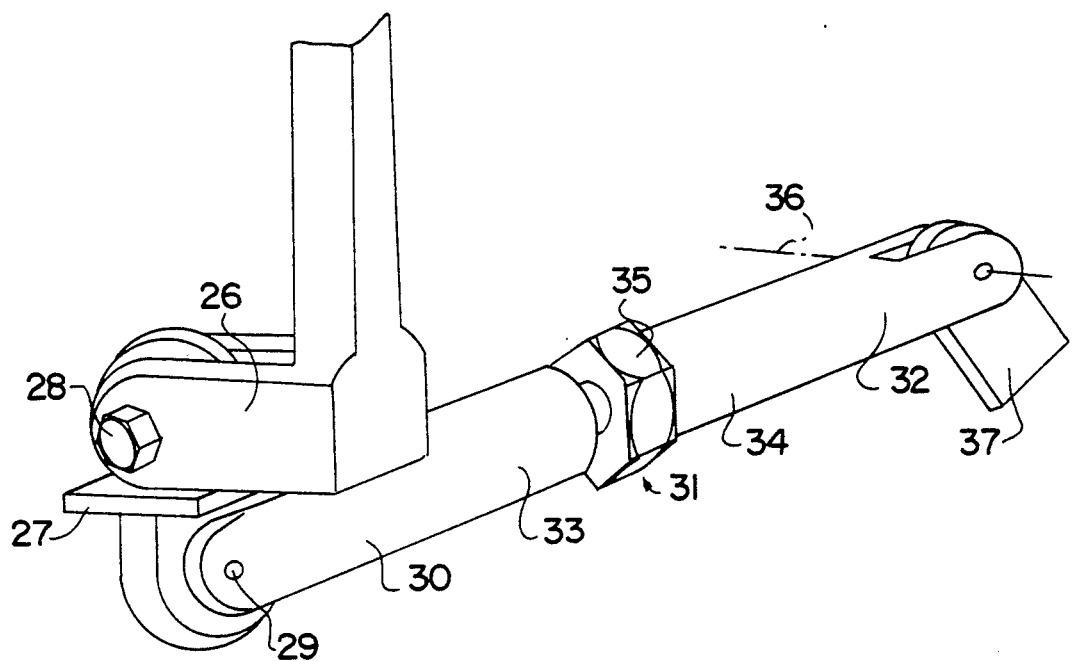
Figure 4:
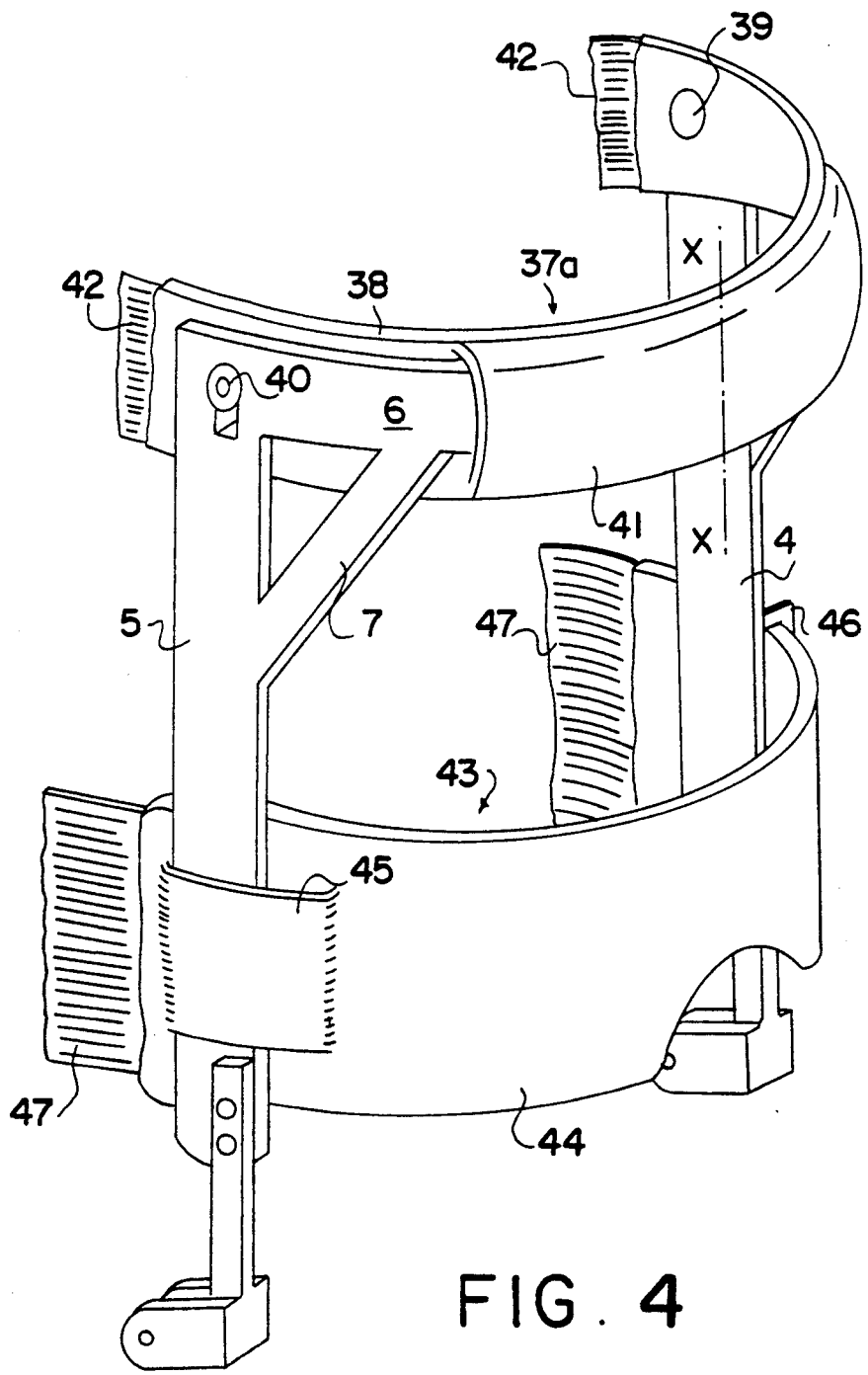

The above-mentioned characteristics of the invention, as well as others will become clearer upon reading the following description of an embodiment, the description being made in conjunction with the following drawings among which:

FIG. 1 is a perspective view of a brace in the bent position, in accordance with the invention, 31 FIG. 2 is a perspective view, on a reduced scale, of the brace shown in FIG. 1 extended, FIG. 3 is an enlarged perspective view of the internal articulation of the brace, and FIG. 4 is a view of the thigh restraining component provided with specially designed binding parts.

The brace in the invention has an upper component 1 to restrain the thigh, a lower component 2 to restrain the leg, and an articulation apparatus 3 between the two restraining components.

The thigh restraining component 1 is made up of two lateral mounts 4 and 5 and a frontal brace 6 welded by its ends to the upper ends of the mounts. The brace 6 has an articulation around an X-X axis in its central portion allowing the mounts 4 and 5 to open more or less. However, the articulation does not allow any translations of one of the mounts 4 and 5 with respect to the other.

A triangulation bar 7 is provided between each mount 4 or 5 and the brace 6 to give more rigidity to the arrangment. Along each mount, is fixed two loops 8 for the passing of straps. The upper strap, at the level of the brace 6, is large and slightly elastic. The lower strap, narrower, passes behind the thigh, 2 to 3 cm above the knee level. In a preferred embodiment of the invention, brace 6 is applied to the second upper third of the thigh. More elaborate binding mechanisms than simple straps can be provided, which will be described in greater detail below, in relation to FIG. 4.

Close to their lower ends, the mounts 4 and 5 have two longitudinal rows of equally spaced holes 9 on the articulation apparatus 3. This gives the freedom of adjusting over a few centimeters the length of the mounts 4 and 5.

The leg restraining component 2 is made up of two lateral mounts 10 and 11 united together by two articulated frontal braces 12 and 13, like brace 6, in their central portion around axes Y-Y and Z-Z respectively. The upper brace 12 is applied at the level of the frontal tibial spine. On the internal side, is applied a support area 14, partially represented in FIG. 1, made of soft material and sufficiently large to hook in a comfortable manner on the upper part of the leg muscular contour which is made up of the lateral and twin muscles. The support area 14 can be made up of an appropriate material used in orthopedics. It can in particular be moulded directly on the subject.

The lower brace 13 is placed on the leg. A support area 15 is attached to it, also partially shown in FIG. 1, also moulded, which allows hooking to the upper part of the ankle bone.

Each mount 10 or 11 has two loops 16 at the level of the braces 12 and 13. Two straps pass through the loops 16 to guarantee the maintaining of the component 2 on the member. A problem with the leg brace is the need to prevent it from slipping down during normal motion. Since the leg component, supports the thigh component, it must not move. The solution of support on the two moleoles is satisfactory.

To further improve the binding of the leg restraining component 2, the straps can be spread obliquely by making them, on one side, go through an upper loop and, on the other side, in a lower loop.

The upper ends of the mounts 10 and 11, like the lower ends of mounts 4 and 5, have two longitudinal rows of equidistant holes 17 allowing the riveting of mounts 10 and 11 onto the articulation apparatus 3 with a number of possible settings.

The external mount of the upper restraining component 1 is attached by its lower end to a leg 18 of the articulation apparatus 3, by means of rivets passing through some of the holes 9 selected in relation to the morphology of the subject. The leg 18 extends the mount 4.

A fork joint 19 is welded perpendicularly to its lower end, oriented to the back, FIG. 2. The fork joint has a horizontal transversal articulation axis 20. In practice, the leg 18 and the fork joint 19 are, preferably, a single part.

Between the two arms of the fork joint 19, a leg 21 directed to the bottom is articulated around the axis 20. Just below the fork joint 19, the leg 21 is thickened such as to provide shoulder 22. By lying under the arms of the fork joint 19, the shoulders 22 limit the pivoting of leg 21 toward the front, in respect of the hypertension, FIG. 2. The leg 21 is extended toward the bottom by a threaded rod screwed into a threaded cylindrical piece 23, the other end of which is welded to a leg 24 attached to the mount 10 of the lower component 2 by means of rivets. This link between the leg 21 and the leg 24 allows a slight rotation between them accompanying the automatic rotation of the knee. With a lock nut 21' on the threaded rod of leg 21, the automatic rotation of the knee can be blocked or limited. The system of the knee brace made up of the shoulder 22 and the lower sides of the arms of the fork joint 19 limit the hyper-extension.

The manufacture of this part of the articulation apparatus 3 must meet two essential requirements. It must be rigid and resistance to wear, because the least slack would result in some inefficiency of the brace.

Similarly to the external mount 4, the internal mount 5 is extended towards the bottom by a leg 25 whose lower end has a fork joint 26 oriented horizontally towards the back, FIG. 2, virtually at the same level as the fork joint 19. In the fork joint 26, as we see more clearly in FIG. 3, the upper portion of a cross-piece 27 is articulated around a transversal axis 28. The central part of the cross-piece 27 forms a stop toward the front for the lower edges of the fork joint 26. The knee-brace system thus made limits hyper-extension on the internal side. The lower part of the cross-piece 27 is articulated around an axis 29 perpendicular to axis 28, carried by a fork joint 30. The fork joint 30 is at the end of a rod 31, the other end of which also has a fork joint 32 whose slot is somewhat parallel to that of fork joint 30. The cross-piece 27 makes up a Cardan setup, together with leg 26 and rod 31. The rod 31 has a part 33 extended by a threaded rod and a bolted part 34 to receive the threaded rod. The part 33 and the part 34 thus have a small amount of rotational play between them, like legs 21 and 24. This slight play accompanies, on the internal side, the automatic rotation of the knee. A lock-screw 35 screwed on the threaded rod of part 33 allows blocking or limiting, on the internal side, of automatic rotation of the knee. Of course, the settings of lock-nut 21' and lock-nuts 35 are complementary.

On the external side, after having unmounted axis 20, one can change the length of the . arrangement formed of legs 21 and 23 by more or less screwing the threaded rod extending leg 21 into leg 23. Similarly, on the internal side, after having removed the axle 28, one can set the length of the rod 31. Once the axles 20 and 28 are remounted, the lengths of the set of legs 21 and 23, on one hand, and of the rod 31, on the other hand, are defined, within the limit of slight play in rotation. These two arrangements of combined lengths allow the carrying out of corrections of the valgus-varus. They also allow the provision of precise correspondence of the axis of the brace with the articular axis. One can also make these changes in length by selecting the rod 31 and leg 21-23 from an assortment of fixed length pieces. The rotation could be guaranteed by manufacturing the pieces from a material having suitable torsion characteristics.

In the fork joint 32, around an axis somewhat parallel to axis 29, is articulated the upper end of a leg 37 whose lower end, after bending 90°, is riveted to mount 11.

The articulation system may have, among other things, means that are not shown, to limit the extension or the bending of the brace.

Furthermore, the thigh restraining element 1 will preferably have binding components especially chosen for the comfort and efficiency of the brace. Such binding components are shown in FIG. 4.

The upper binding component 37a has a front band 38 applied on the internal side of brace 6. The band 38 is slightly larger than brace 6 and it has, on the thigh side, a suitable soft cover, for example of polyethylene. The band 38 is attached at 39 to the end of the brace 6 adjacent to external mount 4 and at 40 to the other end of the brace, adjacent to internal mount 5. At 40, the binding allows a slight play, in the axis of the thigh, between the brace 6 and the band 38. Preferably, the band 38 has a sleeve 41 in its central part, in which the central part of the brace 6 goes through. The opening of the sleeve 41 is wider than the band 38, such as to allow relative motion between the brace and the band, mentioned above. At its ends, the band 38 is extended by straps 42 provided with conventional means of tightening and binding. Preferably, the straps 42 have elasticity for reasons of comfort and the means of tightening and binding are of the VELCRO TM type.

The lower binding component 43 has a wide band 44, provided on the thigh side, like band 38, with a soft cover. On the internal side, the band has on its external side a sleeve 45 whose axis is somewhat parallel to that of the thigh. The internal mount 5 goes through the opening of sleeve 45. The opening of sleeve 45 is slightly larger than mount 5, such that it can move towards the front or the back, as well as longitudinally with respect to the thigh. However, the mount 5 has no play in the radial direction within the sleeve 45.

On the external side, the mount 4 has a loop 46 on its external side, in which the band 44 passes. Like band 38, the band 44 is extended by straps 47 provided with tightening and binding means. Preferably, the lower portion of the band has a notch in its central part to free the knee-cap.

Such binding components improve slightly the comfort of the brace. Furthermore, they allow maintenance of the external mount well in place with respect to the thigh while mount 5 can move slightly in well determined authorized segments.

The articulation system allows the brace to adapt itself perfectly to the varying muscular volumes of the periarticular muscles in the knee, in particular during incomplete bending which has a tendency to spread the external and internal articulations. It also gives a great freedom of motion, like sitting with legs crossed for example, which is of interest in respect of sport activities.

The brace of the invention can be used in practically all cases of instability of the knee. Its various settings and the design of the thigh and leg restraining components allow it to be tailored to the subject under optimal tolerance and comfort conditions. Its articulation apparatus is simple and thus reliable. It is also not cumbersome.

The applications of the brace are also varied: to prevent irregular motion of the knee, carry out valgus or varus corrections, treat knee arthrosis, relieve ill regions by unloading them, re-educate the proprioceptive muscles after removal of a cast, allow a controlled mobility and to protect a knee after ligamentary surgery of the knee, etc.

I claim:

1. An orthopedic apparatus for supporting an unstable knee following an articular ligamentary, neurological or muscular injury, said apparatus comprising an upper component (1) to restrain a thigh and a lower component (2) to restrain a leg below a knee, each of said components having an external and internal vertical member (4, 5, 10, 11) joined by generally arcuate brace means (6, 12, 13), articulated joints (19, 31) formed between said vertical members (4, 10 and 5, 11) of said upper and lower components (1, 2), a first of said articulated joints between said internal members (5, 11) including a first rod 31 having means for adjusting the length of said first rod, said first rod being connected at one end to said vertical member (11) of said lower component (2) and articulated along a first elongated axis (36) of rotation positioned parallel to a direction in which a foot of a person wearing said apparatus moves as the wearer walks, an opposite end of said rod (31) connected to said vertical member (5) of said upper component (1) by a second axis of rotation (28), positioned perpendicular said first axis of rotation, a second of the articulated joints (20, 21) between said external vertical members comprising a second rod (23) having means for adjusting the length of said second rod, said second rod being joined between said external vertical members (4, 10) by an axis of rotation (at 21) in line with said second axis of rotation.

2. An orthopedic apparatus in accordance with claim 1, characterized in that the articulated joints are fork joint articulations.

3. An orthopedic apparatus in accordance with one of the claims 1 or 2 characterized in that said orthopedic apparatus has a center and is articulated at said center.

4. An orthopedic apparatus in accordance with one of the claims 1 or 2 characterized in that said arcuate brace means (12, 13) joining said internal (11) and external (10) vertical members of said lower component (2) comprises two arcuate braces (12, 13).

5. An orthopedic apparatus in accordance with one of the claims 1 or 2 characterized in that the upper component (1) has a first and a second triangulation bar (7) said first triangulation bar (7) joining said internal vertical member (5) and arcuate brace means (6) of said upper component (1), and said second triangulation bar (7) joining said external vertical member (4) and arcuate brace means (6) of said upper component (1).

6. An orthopedic apparatus in accordance with one of the claims 1 or 2 characterized in that said lower component (2) has an internal surface, two support areas (14, 15) being mounted on said internal surface, said support areas (14, 15) comprising soft material.

7. An orthopedic apparatus in accordance with claim 6, characterized in that
said two support areas comprising an upper support area (14) and a lower support area (15);
said arcuate brace means (12, 13) joining said internal (11) and external (10) vertical members of said lower component (2) comprises two arcuate braces, an upper arcuate brace and a lower arcuate brace, each having an internal surface; said upper support area (14) attached to said internal surface of said upper arcuate brace (12), and said lower support area (15) attached to said interior surface of said lower arcuate brace (13) so that said lower support area (15) engages a wearer's upper moleoles.

8. An orthopedic apparatus in accordance with claim 6, characterized in that said support areas (14, 15) comprise molded portions of said soft material, said support areas (14, 15) attached to said internal surface of said lower component (2) on said arcuate brace means, said support areas (14, 15) engaging a wearer's leg.

9. An orthopedic apparatus in accordance with one of the claims 1 or 2 characterized in that said orthopedic apparatus excluding means to limit movement of said articulated joints.

10. An orthopedic apparatus in accordance with one of the claims 1 or 2 characterized in that the upper component (1) has an upper binding (37a) having a first front band (38) with a soft cover (41) which is wider than said arcuate brace means (6) between said vertical members of said upper component, said front band attached to ends of said upper component (1) arcuate brace means (6), an end binding (40) on an interior of said upper component (1) arcuate brace means for allowing a slight longitudinal motion of said upper component (1) arcuate brace means (6) with respect to the upper component interior vertical member, and a lower binding (43) having a second front band (44) with a soft cover, a part of said second front band engaging an inside of a wearer's thigh, a sleeve (45) on said second band, the interior vertical member (5) of said upper component passing through the sleeve (45), said sleeve (45) having a width larger than the width of the interior vertical member (5), such that said second band can move slightly towards the front or the back, as well as longitudinally with respect to the thigh, a loop attached on the exterior of said external vertical member of said upper component, the second front band (44) passing through said loop (46), said first and second bands (36 and 44) having ends extended by straps (42, 47) having tightening and binding means.

11. An orthopedic apparatus in accordance with claim 10, characterized in that the first front band (38) has in a central part having a second sleeve (41) through which said upper component arcuate brace means (6) passes said second sleeve having an opening width greater than a width said upper component (1) arcuate brace means (6), so that said upper component arcuate brace means can slightly move longitudinally with respect to the wearer's thigh.

12. An orthopedic apparatus in accordance with claim 10 characterized in that the straps (42, 47) of said first and second bands (37, 43) have some elasticity in order to improve comfort.

13. An orthopedic apparatus in accordance with claim 10 characterized in that the second front band (44) has a notch to arch over a wearer's knee cap.

14. An orthopedic apparatus in accordance with claim 1 or claim 2, characterized in that said means for adjusting the length of said first rod (31) of said articulation joint between said internal vertical members (5, 11) and said second rod (23) of said articulation joint between said external vertical members (4, 10) each comprises a first part and a second part (33, 34, and 21, 23, 24), said first parts each having a threaded stem, said second parts each having a threaded end, said threaded stems being screwed into said threaded ends.

15. An orthopedic apparatus in accordance with claim 14, characterized in that said threaded stems (21, 23, 24, 31) each have lock-nuts (21', 35) for blocking or limiting rotation of said first parts with respect to said second parts.

* * * * *